United States Patent [19]

Varga et al.

[11] Patent Number: 5,196,478
[45] Date of Patent: Mar. 23, 1993

[54] IMMOBILIZATION OF LIGANDS BY RADIO-DERIVATIZED POLYMERS

[75] Inventors: Janos M. Varga; Peter Fritsch, both of Innsbruck, Austria

[73] Assignee: Epipharm Allergie-Service Gesellschaft M.B.H., Linz, Austria

[21] Appl. No.: 507,348

[22] Filed: Apr. 9, 1990

[30] Foreign Application Priority Data

Aug. 21, 1989 [AT] Austria .................. A 1976/89

[51] Int. Cl.$^5$ .................. C08J 7/12; C08J 7/00; C07K 17/06; C12N 11/06; G01N 33/543; C12O 1/68

[52] U.S. Cl. .................. 525/54.1; 525/54.2; 525/54.21; 525/54.23; 525/54.24; 525/54.26; 525/54.3; 525/54.31; 522/113; 522/114; 522/116; 522/117; 522/126; 522/134; 522/135; 522/136; 522/137; 522/145; 435/177; 435/180; 435/181; 530/402; 530/810; 530/812; 530/815; 530/816; 424/85.8; 424/85.91

[58] Field of Search .................. 525/54.1, 54.2, 54.21, 525/54.23, 54.24, 54.26, 54.3, 54.31; 522/113, 114, 116, 117, 126, 134, 135, 136, 137, 145; 435/177, 180, 181; 530/402, 810, 812, 815, 816; 424/85.8, 85.91

[56] References Cited

U.S. PATENT DOCUMENTS

| | | | |
|---|---|---|---|
| 3,709,844 | 1/1973 | Henich et al. | 521/77 |
| 4,039,413 | 8/1977 | Kraemer et al. | 522/13 |
| 4,046,723 | 9/1977 | Dorman et al. | 524/498 |
| 4,111,838 | 9/1978 | Schaeffer et al. | 252/430 |
| 4,235,973 | 11/1980 | Tschang et al. | 521/146 |
| 4,266,030 | 5/1981 | Tschang et al. | 435/180 |
| 4,415,665 | 11/1983 | Mosbach et al. | 435/179 |
| 4,582,875 | 4/1986 | Ngo et al. | 525/54.1 |
| 4,716,122 | 12/1987 | Scheefers | 436/532 |
| 4,737,544 | 4/1988 | McCain et al. | 525/54.1 |

FOREIGN PATENT DOCUMENTS

| | | |
|---|---|---|
| 1223859 | 4/1984 | Canada. |
| 0050515 | 4/1982 | European Pat. Off. . |
| 0155252 | 9/1985 | European Pat. Off. . |
| 0175973 | 4/1986 | European Pat. Off. . |
| 0278183 | 8/1988 | European Pat. Off. . |
| 0297795 | 4/1989 | European Pat. Off. . |
| 0319957 | 6/1989 | European Pat. Off. . |
| WO87/02619 | 10/1986 | World Int. Prop. O. . |

OTHER PUBLICATIONS

Ugelstad, J., et al., "Swelling of Oligomer-Polymer Particles, New Methods of Preparation of Emulsions and Polymer Dispersions," Advances in Colloid and Interface Science, vol. 13, 1980, pp. 101-140.

Cram, D. J., et al., Organic Chemistry, McGraw-Hill Book Company, Inc., New York, 1959, pp. 574-577.

Colowick, S. P. and Kaplan, D. O. (Eds.), Methods in Enzymology, Academic Press, Inc., New York, 1974, pp. 3-30, 356-376.

Butler, J. E., et al., "The Immunochemistry of Solid—Phase Sandwich Enzyme-Linked Immunosorbent Assays," Fed. Proc., vol. 46, 1987, pp. 2548-2556.

Ceska, M. et al., "Radioimmunosorbent Assay of Allergens," J. Allerg. Clin. Immunol., vol. 49, 1972, pp. 1-9.

Chu, V. P., et al., "Protein-Reactive, Molded Polystyrene Surfaces Having Applications to Immunoassay Formats," J. Appl. Polymer Sci., vol. 34, 1987, pp. 19197-1924.

(List continued on next page.)

Primary Examiner—Nathan M. Nutter
Attorney, Agent, or Firm—Pennie & Edmonds

[57] ABSTRACT

This invention relates to radio-derivatized polymers and a method of producing them by contacting non-polymerizable conjugands with radiolysable polymers in the presence of irradiation. The resulting radio-derivatized polymers can be further linked with ligands of organic or inorganic nature to immobilize such ligands.

32 Claims, 2 Drawing Sheets

OTHER PUBLICATIONS

Larson, P. H., et al., "Covalent Binding of Proteins to Grafted Plastic Surfaces Suitable for Immunoasays," J. Immunol. Methods, vol. 98, 1987, pp. 129–137.

Lloyd, W. G. et al., "Nucleophilic Displacements Upon Poly(Vinylbenzyl Chloride)", J. Appl. Polymer Sci., vol. 7 1963, pp. 2025–2037.

Lowe, C. R., "Some Parameters Relevant to Affinity Chromatography on Immobilized Nucleotides," Biochem. J., vol. 133, 1973, pp. 499–514.

Lowe, C. R., et al., "Affinity Chromatography of Lactate Dehydrogenase on Immobilized Nucleotides," Biochem. J., vol. 133, 1973, pp. 499–514.

Lowe, C. R., et al., "Affinity Chromatography of Lactate Dehydrogenase on Immobilized Nucleotides," Biochem. J., vol. 133, 1973, pp. 515–520.

Lowe, C. R., et al., Affinity Chromatography, J. Wiley and Sons, New York, 1974, pp. 22–31, 74–81, 200–239.

Pal, S. B. (Ed.), Reviews in Immunoassay Technology, MacMillan Press, London, 1988, pp. 1–11.

Varga, J. M., "Hormone-Drug Conjugates," Methods Enzyme, vol. 112, 1985, pp. 259–269.

Wilske, J., et al., "Energy Transfer and Radiolytic Product Formation in the System Polystyrene-Pyrene," J. Polymer, Sci., vol. 7, 1969, pp. 995–1010.

IMMOBILIZATION OF LIGANDS BY RADIO-DERIVATIZED POLYMERS

BACKGROUND OF THE INVENTION

There is a need for covalent modification of polymer surfaces to be used as carriers of molecules, as support for cells or as sorbents in separation methods. The limitations of adsorptive coating of polystyrene, herein referred to as PS, which can be used, for example, as microtiter plates or for bio-assays, are generally known and the need for covalent coupling methods is recognized in the art.

Functionalized PS suitable for covalent attachment of ligands and antibodies has been obtained by the following three methods: copolymerization of monomers containing functional groups as disclosed in Lloyd and Durscher, J. Appl. Polymer. Sci., Vol. 7, 1963, pp. 2025-2037; chemical modification of PS products as taught by Chu and Tarcha, P. J., J. Appl. Polymer. Sci., Vol. 34, 1987, pp. 1912-1924, and graft-polymerization of unsaturated monomers as demonstrated in EP 0 106 169. One problem with these procedures is that the resulting products have impaired optical qualities and/or high background noise in binding assays.

Only the last method involving graft-polymerization of unsaturated monomers uses radiation to initiate covalent bond formation between the support material and the spacer or molecules to be immobilized. Radiation graft-polmerization uses polymerizable monomers to build up a chain in a radiation-initiated or free radical polymerization reaction. The disadvantages associated with radiation graft-polymerization are as follows: 1) Graft-polymerization is technically difficult to do and it is not easy to control, i.e., the length of the grafted polymer is variable; 2) During the process of graft-polymerization other reactions, such as cross-linking of the grafted polymer chain may take place in addition to polymerization resulting in a rigid radiation-grafted layer of polymer; 3) In cases when the ligating group is attached only to the end of the grafted chain, graft-polymerization is not expected to yield high capacity of support; 4) Since in ligandantibody interactions approximately 10 Å length spacers have been found optimal, See Lowe et al., Biochem. J., Vol. 133, 1973, pp. 499-514, the long (hundreds to thousands of monomer-length) grafted chains obtained in EP 0 106 769 are suboptimal; 5) In most graft-polymerization methods large areas of charged and/or hydrophobic surfaces are introduced, leading to high levels of nonspecific interactions and unacceptable background noise, See, Lowe and Dean, P.D.G. Affinity Chromatography, J. Wiley and Sons, N.Y. 1974. These disadvantages of radiation graft-polymerization can be circumvented by using nonpolymerizable molecules for radiation-mediated derivatization of polymers as described below.

SUMMARY OF THE INVENTION

The invention relates to a method of using nonpolymerizable small molecules in the radiation-mediated derivatization (radio-derivatization) of polymers. When polymers such as molded PS products (e.g. microtiter plates) or latex particles are irradiated with high energy (1-10 Mrads) gamma rays in the presence of nonpolymerizable small molecules, such as aromatic amines, some of these molecules incorporate into the polymer leading to the formation of radio-derivatized polymer, which is herein referred to as RDP. Having improved adsorptive and ion-binding characteristics, RDPs can be used directly as cell/tissue culture substrates, ion-exchangers, or sorbents for chromatography.

This invention further relates to RDPs suitable for introducing anchoring groups to be used for covalent immobilization or fixing of molecules on polymer surfaces. Two classes of RDPs can be identified regarding their ability for covalent immobilization of biologically important molecules: 1) reactive RDPs, which are able to form covalent bonds with molecules such as proteins without the help of cross-linkers and 2) functionalized RDPs, which can be used for the immobilization of molecules with activators (e.g. carbodiimides) or with cross-linkers.

It is an object of the present invention to produce solid, low-noise supports having favorable adsorptive characteristics for binding assays. Most of the RDPs can be produced without the impairment of the optical quality of transparent polymers, e.g. PS, thereby making derivatized microtiter plates suitable for colorimetric assays. RDPs in particle form are suitable for the preparation of affinity sorbents, e.g., for high performance affinity chromatography and for the immobilization of enzymes.

BRIEF DESCRIPTION OF THE DRAWINGS

FIG. 2 is explained in more detail in Example 4.

DETAILED DESCRIPTION OF THE PREFERRED EMBODIMENT

Figure 1:
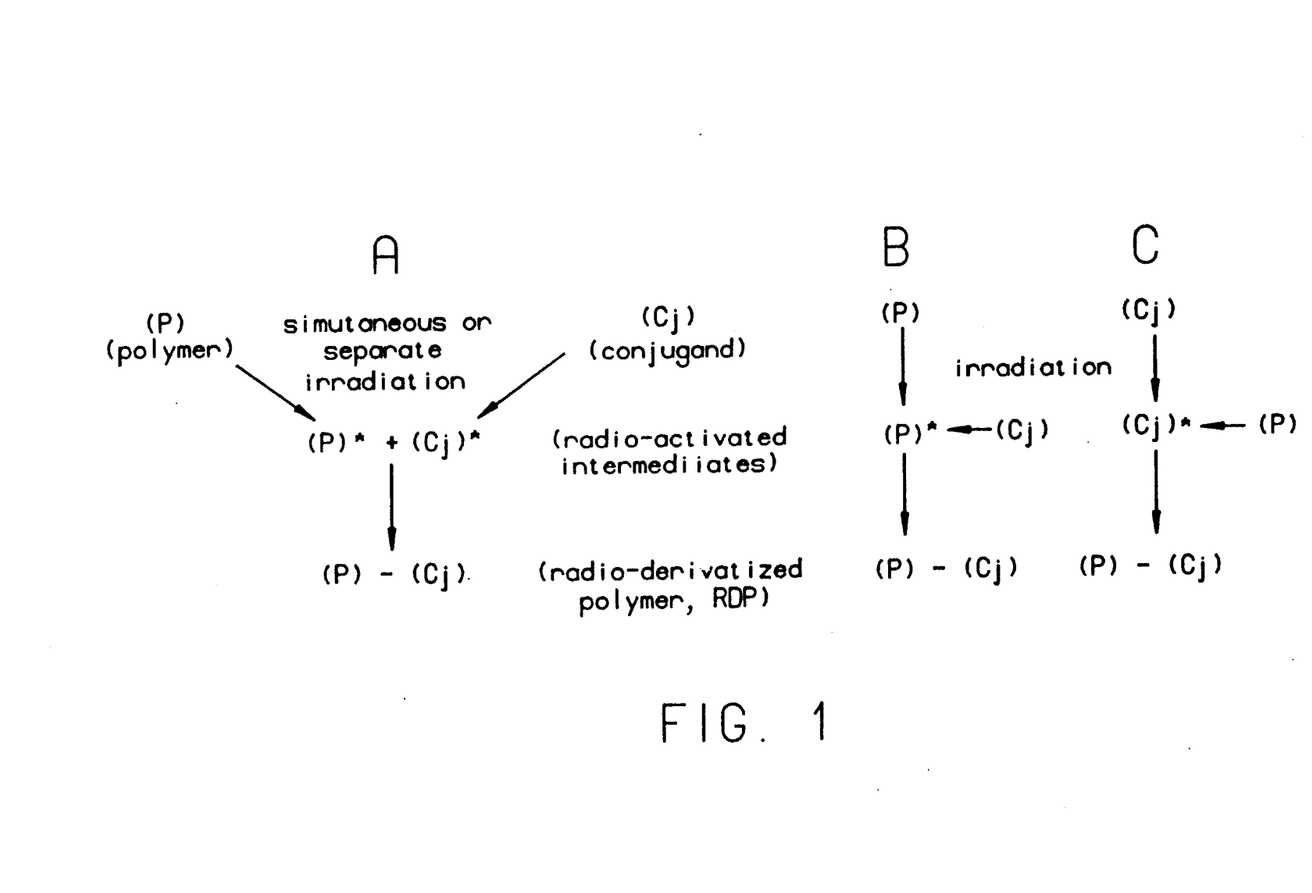
FIG. 1 shows the basic principles of radioderivatization according to this invention and the four ways of obtaining radio-derivatization polymers.

The principles of the present invention are illustrated in FIG. 1. The term radio-derivatization describes the radiation-mediated stable attachment of nonpolymerizable molecules to polymers. Within this term, "radio-" stands for irradiation in the same way as radiotherapy. In schemes A, B, and C of FIG. 1, [P] can be any polymer that contains radiolysable bonds. Conjugands, designated as [Cj], can be any compound containing radiolysable bonds. In particular, aromatic compounds are preferable with polystyrene. Radio activated intermediates [P]* and [Cj]* can be free radicals and/or other reactive intermediates of [P] and [Cj] that in recombinations, condensations or other types of reactions lead to the formation of radio-derivatized products.

The radio-derivatized polymer (RDP) is represented as [P]-[Cj], which is a collective term to denote the union of [P] and [Cj] supposedly by covalent bond formation. Even if non-covalent interactions—such as entrapment of Cj in P—contribute to the formation of some of the radio-derivatives, these have been shown to be stable enough for the immobilization of molecules for being practically useful in solid-phase assays (Example 22). Reactive RDPs are those RDPs that are able to form stable bond(s) with molecules of practical importance such as ligands, antibodies and enzymes in the absence of activators or cross-linkers. Functionalized RDPs are RDPs carrying functional groups such as nucleophiles. Additional substances such as activators or cross-linkers are needed for the covalent attachment of molecules of practical importance to functionalized RDP.

Radio-derivatization can be carried out in four different methods, each of which is believed to result in the formation of the same RPD. Two methods are depicted in FIG. 1A, firstly, simultaneous radio-derivatization wherein [P] and [Cj] are irradiated in close contact with each other (i.e., microtiter plate wells containing a solution of Cj) and, secondly, separate radio-derivatization wherein [P] and [Cj] are irradiated separately to form [P]* and [Cj]*, which are then brought into contact. A third approach is shown in FIG. 1B wherein only [P] is irradiated to form [P]* which is then exposed to [Cj]. FIG. 1C shows a fourth way wherein only [Cj] is irradiated to form [Cj]*, which is then exposed to [P].

While the examples described herein were all performed using the simultaneous method (FIG. 1 A), any of the other three approaches can be used. The formation of stable, long-lasting radicals and/or other reactive intermediates during high energy irradiation is well known (hexadienylradicals, formed from polystyrene by high energy gamma radiation may survive for months, i.e., the half-life of these radicals is approximately one-half year. See Wilske and Heusinger, J. Polymer. Sci., Vol. 7, 1969, pp. 995-1010). The sequential process(es) may be preferred when the structural integrity of [Cj] or [P] is to be preserved.

The polymers of this invention are those polymers containing radiolysable bonds, which undergo radiolysis under the conditions of radio-derivatization. In the context of this invention, radiolysable means sufficient susceptibility to radiolysis to provide activated foci on the surface of a polymer in densities to allow coating of the plate with approximately 100 p. moles/cm$^2$ anchoring functions when irradiated at doses of 1-10 Mrads. Although the preferred polymer in this invention is polystyrene and its co-polymers, other suitable radiolysable polymers include acetal resins, acrylics and their co-polymers, alkyl resins, cellulose acetate, coumarone-indene resins, epoxy resins, furane resins, melamine resins, paracoumarone-indene resins, pentaerythritol resins, phenolics and their copolymers, polyesters and their co-polymers, polyethylene, and its copolymers, polypropylene and its co-polymers, polyamides (nylon, etc.), polybutadienes and their co-polymers (butadiene-styrene), polyethylene glycols, polyvinyl alcohol and its co-polymers, polyvinyl chloride and its co-polymers, polyvinyl acetate and its co-polymers, polyphtalates and their co-polymers, polyurethane and its co-polymers, polyisoprene and its co-polymers, silicones and urea-formaldehyde polymers.

The term "conjugand" as used herein, is a collective term that refers to the nonpolymerizable compound that is initially linked to the polymer to form the RDP in radio-derivatization. These nonpolymerizable compounds are chemically pure and contain radiolysable bonds. The term radiolysable is defined above and the term nonpolymerizable as used herein means a compound that does not undergo polymerization—or if it does, polymerization occurs as an unintended side reaction—during exposure to high-energy irradiation.

Depending on the type of conjugand used, the present invention produces two classes of RDPs: reactive RDPs and functionalized RDPs. Reactive RDPs can be used for the immobilization of molecules such as proteins without activators or cross-linkers. They can be produced by generation of reactive groups on the polymers from nonreactive components during the process of radio-derivatization as in Example 3, Table 3. The exact chemical nature and mechanisms for the formation of these products is unknown. However, without being bound by theory, it is believed that during irradiation of polystyrene in the presence of water, oxygen and aromatic compounds, such as p-aminophenol or 2-amino-4-Cl-phenol, protein-reactive groups, such as aldehydes and/or quinones are generated. Reactive RDPs can also be obtained by radio-derivitization with radiation-resistant acid-halides, acid-azides or active esters that are able to react with suitable functions such as nucleophilic groups present on proteins and other biologically important molecules. Reactive RDPs can also be produced by the activation of functionalized RDPs.

Reactive RDPs can be prepared by irradiating polymers in the presence of nonpolymerizable conjugands that are quinones or compounds from which quinones or quinoid structures are generated during radio-derivatization. General examples of such conjugands are aromatic polyols, amino-phenols and certain aromatic diamines. Particularly preferred conjugands in this class are p-aminophenol, 2-amino-4-Cl-phenol and 5-I-2-amino-pyrimidin. Specific examples of reactive RDP forming conjugands which are quinones or compounds from which quinones are generated are: acenaphtene quinone, acetyl pyrocatechol, 4-acetyl pyrogallol, alizarin, 3-amino alizarin, 4-amino alizarin, 2,3-dihydroxy aniline, 3,4-dihydroxy aniline, 1,2-dihydroxy anthracene, 9,10-dihydroxy anthracene, 9,10-anthraquinone, 1-amino-9,10-anthraquinone, 2-amino-9,10-anthraquinone, 1-bromo-9,10-anthraquinone, 2-bromo-9,10-anthraquinone, 1-chloro-9,10-anthraquinone, 2-chloro-9,10-anthraquinone, 1-hydroxy anthraquinone, 2-hydroxy anthraquinone, 1,4-dihydroxy anthraquinone, 4,5-dihydroxy anthraquinone, 3,4-dihydroxy benzaldehyde, 1-chloro 2,3-dihydroxy benzene, 4-chloro 1,2-dihydroxy benzene, 1,2-diamino benzene, 1,4-diamino benzene, o-aminophenol, p-aminophenol, 3,4-diamino benzene sulfuric acid, 2,3-diamino benzoic acid, 2,3-dihydroxy benzoic acid, 3,4-diamino biphenyl, 3,4-dihydroxy benzoic acid, 2,3-dihydroxy benzophenone, chloranil, chloranilic acid, catechol, homogentistic acid, hydroquinone, 2-acetyl hydroquinone, isatin, 9,10-naphthacene quinone, 9,11-naphthacene quinone, 1,4-diamino naphthalene, 1,2-diamino naphthalene, 2,3-diamino naphthalene, 1,4-diamino-2-methyl naphthalene, 1,2-dihydroxy naphthalene, 1,4-dihydroxy naphthalene, 2,3-dihydroxy naphthalene, 1,2-naphthoquinone, 3-bromo 1,2-naphthoquinone, 4-bromo 1,2-naphthoquinone, 6-bromo 1,2-naphthoquinone, 3-chloro 1,2-naphthoquinone, 3,6-dibromo 1,2-naphthoquinone, 4,6-dibromo 1,2-naphthoquinone, 6-hydroxy 1,2 naphthoquinone, 7-hydroxy 1,2-naphthoquinone, 3-methyl 1,2 naphthoquinone, 4-methyl 1,2-naphthoquinone, 1,4-naphthoquinone, 2-chloro 1,4-naphthoquinone, 5-chloro 1,4-naphthoquinone, 6-chloro 1,4-naphthoquinone, 2,6-dichloro 1,4-naphthoquinone, 5,6-dichloro 1,4-naphthoquinone, 5,8-dichloro 1,4-naphthoquinone, 5,8-dihydroxy 1,4-naphthoquinone, 2,5-dimethyl 1,4-naphthoquinone, 2,6-dimethyl 1,4-naphthoquinone, 2,8-dimethyl 1,4-naphthoquinone, 2-ethyl-1,4-naphthoquinone, 2-hydroxy 1,4-naphthoquinone, 5-hydroxy 1,4-naphthoquinone, 6-hydroxy 1,4-naphthoquinone, menadione, 2-phenyl 1,4-naphthoquinone, nitranilic acid, naphthopurpurin, 3,4-dihydroxy phenanthrene, 9,10-phenanthraquinone, 1,2-dihydroxy 9,10-phenanthraquinone, 2-hydroxy 9,10-phenanthraquinone, 4,5-dihydroxy, 9,10-phenanthraquinone, 3-hydroxy, 9,10-phenanthraquinone, o-quinone, 3-chloro o-quinone, 4-chloro o-quinone, p-quinone, 2-chloro p-quinone, toluquinone, phenyl p-quinone, 2,3-benzothio phenequinone, thiosatin, 2,3-dihydroxy toluene, and 3,4-dihydroxy toluene.

In addition to the above, conjugands that are protein modifying reagents can be used to prepare reactive RDPs.

Generally, protein modifying reagents that are known in the art can serve as conjugands for preparing reactive RDPs. Specific examples of suitable protein modifying reagents are: acetic anhydride, acetaldehyde, acetaldehyde bis(2-chloroethyl)acetal, acetaldehyde diacetal, acetaldehyde dimethyl acetal, trichloro acetal, acetaldehyde bromodiethylacetal, acetaldehyde chlorodiethylacetal, dichloro acetaldehyde, trichloro acetaldehyde, acetylacetone, chloroacetone chloroform, acetyl bromide, acetyl chloride, acetyl fluoride, acetic acid bromoethylester, acetic acid chloroethylester, adipaldehyde, adamantyl fluoroformate, 4-amino-4'-dimethylaminobenzene, 5-aminotetrazole, 3-amino-1,2,4-triazole, azobenzene-1-sulfenyl bromide, 1-acetylimidazole, 3-aminophenylboronic acid hemisulfate, N-acetyl-DL-cysteine, N-acetyl-DL-homocysteinethiolactone, 4-amino-phenylmercuric acetate, N-(4-anilino-1-naphtyl)maleimide, azobenzene-2-sulfenyl bromide, 4-azidophenacyl bromide, 1-amino-5-azidonaphthalene, 4-azidoaniline, 4(5)-azidofluorescein diacetate, 5-azido-2-nitrobenzoic acid, 4-azidophenacyl bromide, 4-azidophenyl isothiocyanate, 4-acetamido-4'-isothiocyanatostilbene-2,2'-disulfonic acid, N-(4-aminobutyl)-N-ethylisoluminol, 4-aminofluorescein, 5-aminofluorescein, 7-amino-4-methylcoumarin, 8-anilinonaphthalene-1-sulfonic acid, auramine O, benzonitrile, 4-benzylamino-7-nitrobenzofurazan, benzyl chloroformate, 4-(BOC-2-aminomethyl)phenylisothiocyanate, 5-BOC-2-mercapto-4,6-dimethylpyrimidine, 2-(BOC-oximino)-2-phenylacetonitrile, t-butyl carbazate, (2-bromoctyl) chloroformate, 3-bromopropionic acid, bromoacetic acid, 4-bromophenacyl bromide, 2,3-butanedione, 3-bromo-3-methyl-2-(2-nitrophenylmercapto)3H-indole, N-(4-(2benzimidazolyl)phenylmaleimide, 4,4,-bis (dimethylamino)-diphenyl carbinol, bromopyruvic acid, N butylmaleimide, omega-bromo-4-nitroacetophenone, benzophenone 3,3',4,4'-tetracarboxylic dianhydride, (+)-biotin 4-nitrophenyster, (+)-biotin 4-nitrophenylester, 2,2'-biquinolone-4,4'-dicarboxylic acid, bis(4-fluoro-3-nitrophenyl)sulfone, 1,5-bis(succinimidooxycarbonyloxy) pentane, 4-(BOC-aminoethyl)phenylisothiocyanate, N-BOC-1,6-diaminohexane, N-(4-(2-benzimidazolyl)phenylmaleimide, 2',4'-bis(di(carboxymethyl)aminoethyl)fluorescein, 4,4'-bis(dimethylamino)diphenyl carbinol, 4-bromomethyl-7-methoxy-courmarin, BOC-L-tyrosine hydrosuccinimide ester, benzaldehyde, 2-amino benzaldehyde, 3-amino benzaldehyde, 4-amino benzaldehyde, 2-bromo benzaldehyde, 3-bromo benzaldehyde, 4-bromo benzaldehyde, 2-chloro benzaldehyde, 3-chloro benzaldehyde, 4-chloro benzaldehyde, 2-hydroxy benzaldehyde, 3-hydroxy benzaldehyde, 4-hydroxy benzaldehyde, benzene sulfinic acid chloride, benzene sulfonic acid chloride, benzene sulfonic acid fluoride, benzoyl bromide, benzoyl chloride, benzoyl fluoride, 2-chloro benzoic acid anhydride, 3-chloro benzoic acid anhydride, 3-chloro benzoyl chloride, 4-chloro benzoic acid anhydride, 4-chloro benzoyl chloride, bioxirane, 1,2-butylene oxide, butyric anhydride, butyryl bromide, bis(2-nitrophenyl)disulfide, (bis(trifluoroacetoxy)iodo)-benzene, chloral, chloral alcoholate, chloracetic acid anhydride, chlorodiphenyl acetyl chloride, cumaldehyde, 1,2-epoxy cyclohexane, caprylic anhydride, caprylic chloride, cyclamen aldehyde, 2-chloro-3,5-dinitropyridine, chloro ethanesulfonic acid, 4-chloro-7-nitrobenzofurazan, citraconic anhydride, 2-cyanopyridine, 1,2-cyclohexanedione, 1,1'-carbonyldiimidazole, 1,1'-carbonyldi(1,2,4-triazole), N-cyclohexyl-N'-(2-morpholinoethyl)carbodiimide metho-p-toluenesulfonate, camphorquinone-10-sulfonic acid, chloramine B, chloramine T, N-chlorosuccinimide, cyanuric fluoride, chloranil, chloroethane sulfonic acid, 4-(chlormercuri)-benzenesulfonic acid, 4-(chlormercuri)benzoic acid, 4-chloro-7-sulfobenzofurazan, 1-cyano-4-dimethylaminopyridinium tetrafluoroborate, cystamine, cibacron blue 3G-A, carbethoxymethyl isothyocyanate, diphenylethanal, diphenyl acetic anhydride, diphenyl acetyl chloride, diphenyl carbodiimide, 1,2-diacetylbenzene, N,S-diacetylcysteamine, di-t-butyl dicarbonate, N,N-diethyl-2,4-dinitro-5-fluoroaniline, diethyl pyrocarbonate, 4-dimethylamino-benzene-4,-isothiocyanate, 4-dimethylaminoazobenzene-4,-sulfonyl-chloride, 4-(5-dimethylaminonaphthalene-1-sulfonylamino)-phenylisocyanate, 5-dimethylamino-1-naphthalenesulfonyl chloride, dimethylmaleic anhydride, 3,5-dimethyl-1-pyrazolyl formamidinium nitrate, 2,4-dinitro-5-fluoroaniline, 2,4-dinitro-1-fluorobenzene, N,N'-di-t-butylcarbodiimide, N,N'-dicyclohexylcarbodiimide, N-(dimethylaminopropyl)-N'-ethyl carbodiimide, 2-ethoxy-1-ethoxycarbonyl 1,2-dihydroquinoline, 1,4-dithioerythritol, (−)1,4-dithio-L-threitol, 1,4-dithio-DL-threitol, diisopropylfluorophosphate, 4-dimethylaminoazobenzene-4'-sulfonylchloride, 5-dimethylamino-1naphthalenesulfonylchloride, 4-dimethylamino benzaldehyde, diethyl pyrocarbonate, 1,2-diiodoethane, N-(4-dimethylaminoazobenzene-4,)iodoacetamide, N-(7-dimethylamino-4-methyl-3-coumarinyl)maleimide, 2,2'-dipheyl-1-picrylhydrazyl, 2,2'-dithiobis(4-methylthiazole), 5,5'-dithiobis(2-nitrobenzoic acid), (3,3',6) 2,2'-dithiobis(5-nitropyridine), 2,2,-dithio dibenzoic acid, 2,2'-dithiodipyridine, 4,4'-diazidostylbene-2,2'-disulfonic acid, diethylenetriamine pentaacetic acid dianhydride, diethylene pyrocarbonate, 1,5-difluoro-2,4-dinitrobenzene, 1,6-diisocyanatohexane, dimethyl adipimidate N-(dimethylainopropyl)-N'-ethylcarbodiimide, dimethyl 3,3'-dithiodipropionimidate, dimethylpimelinediimidate, dimethylsuberimidate, 3,3'-dithiodipropionic acid bis(N-hydroxy-succinimide ester), dansylcadaverine, dansylhydrazine, 4-(4,6-dichloro-s-triazin-2-ylamino)-fluorescein, 4-(5-dimethyl aminonaphthalene-1-sulfonylamino)phenylisocyanate, dimethyloxyrane, 4-dimethylamino-1-naphthyl isothiocyanate, diphenylborinic anhydride, (diacetoxyiodo)benzene, 6-diazo-5-oxo-5,6-dihydro-1-naphthalenesulfonylchloride, 2,3-dimercapto-1propanol, 2,4-dinitrophenylhydrazine, 1,6-diphenyl-1,3,5-hexatriene, 1-dodecanethiol, epibromohydrin, alphaepichlorhydrin, beta-epichlorohydrin, epiiodohydrin, epicyanohydrin, ethanesulfonyl chloride, N-ethoxycarbonyl phtalimide, ethyl acetimidate, N-ethylmaleimide, ethyl trifluoroacetate, ethanethiol, ethyl diazoacetate, furfural, 9-fluorenylmethylchloroformate, 5'-(4-fluorosulfonylbenzoyl)adenosine, formaldehyde, 4-formyl-1-methylpyridinium benzenesulfonate, fluorescein mercuric acetate, fluoresceinisothiocyanate, fluoresceinisothiocyanate isomer I, 4-fluoro-3-nitrophenyl azide, N-(3-fluoranthyl)maleimide, fluoresceinamine, 4-fluoro-7-nitrobenzofurazan, fluram, glycolaldehyde, glyoxylic acid, glycolic anhydride, glycidic acid, glycidol, glycinamide, glyoxal, L-glutathione (oxidized), glutaraldehyde, glutaryl chloride, glutaronitrile, 2-hydroxy-5-nitrobenzyl bromide, 6-hydroxy-2-naphthyl disulfide, hexamethylene diisocyanate, 3-(4-hydroxyphenyl)propionic acid N-hydroxysuccinimidester, N-hydroxy sulfosuccinimide, DL-homocysteine thiolactone, 2'-(4-hydroxy phenylazo)-benzoic acid, iodo acetic acid, iodo acetamide, iodo acetid acid ethylester, isobutyryl chloride, isonicotin aldehyde, isonicotinic acid anhydride, 2-iminothiolane, N-iodosuccinimide, N-(iodo acetaminoethyl)-1-naphthylamine-5'-sulfonic acid, iodoacetonitrile, iodomethane, 2-iodobenzoic acid, isatin, isophtalaldehyde, lucifer yellow CH, lucifer yellow VS, methoxy acetyl chloride, metaldehyde, 5,5'-methylene disalicyl aldehyde, methan sulfonyl chloride, methyloxiran, maleic anhydride, mersalyl acid, N-methoxy carbonylmaleimide, 2-(2-(2-methoxyethoxy)ethoxy) acetic acid, methyl isothiocyanate, S-methylisothiourea sulfate, O-methylisothiourea sulfate, O-methylisothiourea hydrogen sulfate, methyl 4-nitrobenzenesulfonate, 2-methoxy-5-nitrobenzyl bromide, 4-maleimidobutyric acid, 6-maleimidocaproic acid, N-maleoyl-beta-alanine, N-(2-mercaptopropionyl)glycine, mercury orange, O-methyl-N-N'-diisopropylisourea, N-methyl maleimide, S-methyl methane thiosulfonate, methyl 4-nitro benzenesulfonate, malononitrile, methyl 4-hydroxybenzimidate, N-methyl mercaptoacetamide, N-methylphenazonium methyl sulfate, O-acetyl mandelyl chloride, methylglyoxal, 2-nitrobenzene sulfenyl chloride, 4-nitrophenyliodoacetate, 2-nitro-5-thiocyanato benzoic acid, 4-nitro-L-tyrosine ethylester, 1-naphthaldehyde, 2-naphthaldehyde, 2-hydroxy-1-naphthaldehyde, alph anaphthyl thiocyanate, beta naphthyl thiocyanate, ninhydrin, 4-nitrophenyl acetate, 4-nitrophenyl formate, N-nitroso-N-methyl-4-toluenesulfonamide, 2-nitrobenzene sulfenyl chloride, 1-hydroxy-2-naphthaldehyde, naphtalic anhydride, naphthalene sulfuric acid chloride, naphthosultone, 1-naphthoic acid anhydride, 1-naphthoic acid chloride, 2-naphthoic acid anhydride, 2-naphthoic acid chloride, octanal, 2-oxoglutaric acid, phenoxy acetic anhydride, phenoxy acetyl chloride, phenyl acetic anhydride, phenyl acetyl chloride, o-phenacyl bromide, m-chloro-p-phenacyl bromide, p-chloro-p-phenacyl bromide, p-bromo-p-phenacyl chloride, phenacyl chloride, phenyl maleic acid anhydride, palmitaldehyde, paraldehyde, pentanal, 4-hydroxy pentanal, 3-hydroxy 2-methyl pentanal, 2-oxopentanal, 4-methyl-2-oxopentanal, 4-oxopentanal, 2-phenyl pentane diic acid, 2-phenyl pentane dioic acid anhydride, 3-phenyl pentane dioic acid anhydride, phtaladehyde, phtaldialdehyde, phtaladehydic acid, phtalic acid anhydride, phtalic acid dichloride, propanal, propanal diethylacetal, 2-bromo propanal, 2-chloro propanal, 3-chloro propanal, 2-chloro-2-methyl propanal, 2,3-dibromo propanal, 2,2-dichloro propanal, 2,3-dichloro propanal, 2-phenoxy propanal, 2-phenyl propanal, 3-phenyl propanal, pivaldehyde, propranolonal, propionic anhydride, propionyl bromide, propionyl chloride, phenyl glycidol, phenyl rhodanate, pentafluorophenyl acetate, phenylisothiocyanate, phenylmethanesulfonyl fluoride, phtalonitrile, pyridoxal hydrochloride, pyromellitic dianhydride, 9,10-phenanthrene quinone, phenylglyoxal, phenylmethanesulfonyl fluoride, D-penicillamine, phenylarsine oxide, N,N'-(1,2-phenylene) dimaleimide, N,N'-(1,4-phenylene)dimaleimide, N-phenylmaleimide, N-propylmaleimide, N-(3-pyrenyl)maleimide, polyethylene glycol 600 diacid, phenacyl bromide, photobiotin, 9,10-phenanthrene quinone, pyridine-4-carboxaldehyde, benzyl rhodanate, phenyl rhodanate, p-tolyl rhodanate, rhodamine b isothiocyanate, succinic anhydride, succinic acid monochloride, benzyl sulfonyl chloride, salicylaldehyde, N-succinimidyl-3-(2-pyridylthio) propionate, 2-sulfobenzoic acid cyclic anhydride, 4-sulfophenyl isothiocyanate, N-succinimidyl 3-maleimidobenzoate, N-succinimidyl 4-maleimidobutyrate, N-succinimidyl 6-maleimidocaproate, N-succinimidyl-3-maleimi dopropionate, sebaconitrile, sulforhodamine 101 acid, sulforhodamine 101 acid chloride, styrene oxide, terephthalaldehyde, p-toluenesulfinyl chloride, o-toluenesulfonyl chloride, p-toluenesulfonyl chloride, 3-tosyloxypropyl isocyanate, trifluoroacetic anhydride, 3-trifluoromethylphenyl isocyanate, 2,2,6-timethyl-1,3-dioxin-4-one, 2,4,6-trinitrobenzenesulfonic acid, triethoxonium tetrafluoroborate, trimethyloxonium tetrafluoroborate, 1-thioglycerol, thioglycolic acid tributylphosphine, N-tosyl-L-lysine chloromethylketone, tosyl-L-phenylalanine chloromethylketone, thiodiethylene glycol, toluylene-2,4-diisocyanate, tetramethylrhodamine B isothiocyanate, 6-(4-toluidino)-2-naphthalenesulfonic acid, 2,2,2-trichloroethanol, toluene sulfonic acid, vanilin, veratrylaldehyde, valeric aldehyde, valeryl chloride, m-xylylene diisocyanate, N-acetyl-beta-glucosamine phenylisothiocyanate, alpha-glucopyranosylphenyl isothiocyanate, beta-glucopyranosylphenyl isothiocyanate, beta-galactopyranosylphenyl isothiocyanate and alphamannopyranosylphenyl isothiocyanate.

Figure 2:
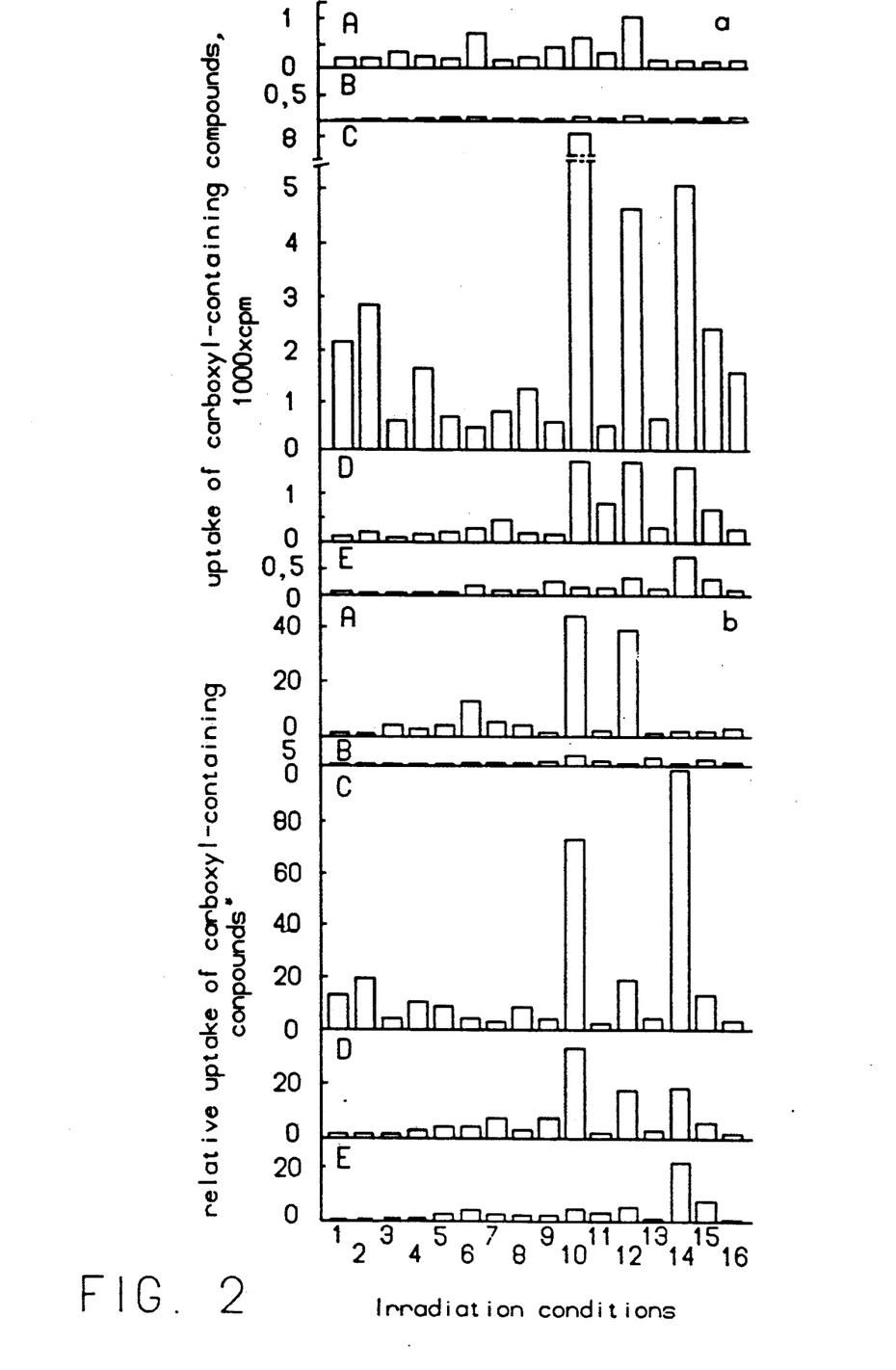
FIG. 2 shows the effects of radioderivatization of polystyrene on the EDC-mediated uptake of five carboxylic acids designated A through E. In the top chart designated (a), shaded histograms show uptake of radio activity without ethyldiethylaminopropyl-carbodiimide (EDC). The lower chart (b) illustrates the relative uptake of radioactivity, which is the ratio of uptake obtained with irradiated plates versus non-irradiated plates in the presence of EDC.

Functionalized RDPs can be obtained by choosing a conjugand with the proper functional group for radio-derivatization. For example, nucleophilized RDPs can be obtained by using nucleophile-containing conjugands. This principle is shown in FIG. 2. When polystyrene is radio-derivatized in the presence of aromatic amines, such as p-aminophenol, DL-2-amino-1 (p-hydroxyphenyl)-ethanol-1 or benzyl esters of amino acids, the resulting RDPs can be used for the coupling of carboxyl-containing compounds with carbodiimide.

The choice of conjugand to make a functionalized RDP depends on the particular functionalization desired. For example, aromatic amines can be used if a functional group capable of being diazotized is desired. When a nucleophile-functionalized RDP is desired, compounds that contain nucleophilic groups such as amino, hydroxyl or mercapto groups should be used as the conjugand. The preferred conjugands in this class are amines which contain aromatic structures, but not necessarily aromatic amines. Examples of these preferred conjugands are anilin and its deriviatives (e.g., m-phenylene diamine), amino phenols (e.g., p-amino phenol), naphthylamines (e.g., 1,2,naphthylene diamine) aromatic esters of aminoacids (e.g., L-serine benzyl ester) and compounds that contain different nucleophile such as 2-amino 1(4-hydroxyphenyl)ethanol-1 (AHE). Specific examples of suitable nucleophile-containing conjugands for preparing nucleophile-functionalized RDPs are: thionalide, thioglycolic acid anilide, p-acetyl phenol, o-mercapto anilin, m-mercapto anilin, p-mercapto anilin, 1-hydroxy anthracene, 2-hydroxy anthracene, 9-hydroxy anthracene, 3-hydroxy azobenzene, 4-hydroxy azobenzene, m,m'-methylene diphenol, p,p'-methylene diphenol, 1,5-dihydroxy naphthalene, 1,6-dihydroxy naphthalene, 1,7-dihydroxy naphthalene, 1,8-dihydroxy naphthalene, 2,6-dihydroxy naphthalene, 2,7-dihydroxy naphthalene, 1-hydroxy naphthalene, 2-hydroxy napthalene, 2-hydroxy phenanthrene, 3-hydroxy phenanthrene, 9-hydroxy phenanthrene, phenol, 2-bromophenol, 3-bromophenol, 4-bromophenol, 3-bromo-5-chlorophenol, 4-bromo-2-chlorophenol, 2-chlorophenol, 3-chlorophenol, 4-chlorophenol, 2,4-dibromophenol, 2,6-dibromo phenol, 2,3-dichlorophenol, 2,4-dichlorophenol, 2,5-dichlorophenol, 2,6-dichlorophenol, 3,4-dichlorophenol, 3,5-dichlorophenol, 2-iodophenol, 3-iodophenol, 4-iodophenol, 2-mercaptophenol, 3-mercaptophenol, 4-mercaptophenol, 2-pyridol, 3-pyridol, 4-pyridol, saligenin, alpha-3-dihydroxy toluene, alpha,2-dihydroxy toluene, alpha,4-dihydroxy toluene, 2,4-dihydroxy toluene, 2,5-dihydroxy toluene, 3,5-dihydroxy toluene, 2-hydroxy toluene, 3-hydroxy toluene, 4-hydroxy toluene, tyrosine, and DL-2-amino-1(4-hydroxyphenyl)-ethanol-1.

Specific examples of suitable amino groupcontaining conjugands for preparing functionalized RDPs that are reactive with carboxyl-containing compounds in the presence of activators, such as carbodiimides are: n-butylamine, s-butylamine, t-butylamine, putrescine, cyclohexylamine, ethylamine, ethylene diamine, hexamethylene diamine, 1-amino pentane, 2-amino pentane, 3-amino pentane, cadaverin, phenylalanine, propylamine, isopropylamine, amphetamine, 1,2-propane diamine, trimethylene diamine, DL-alanine, beta alanine, benzylamine, m-bromo benzylamine, p-bromo benzylamine, and triethylene tetramine.

The preferred amino group-containing conjugands suitable for coupling of various carboxyl compounds in the presence of an EDC activator are DL-2-amino-1(4-hydroxyphenyl)-ethan-1-ol, p-aminophenol, 3,4-diamino pyridine, 1-alanine benzyl ester, L-serine benzyl ester (See Example 4, FIG. 2).

The term activators as used herein refers to those types of substances suitable for activating carboxyl groups for peptide synthesis, which include mixed anhydride types, active ester types, hydroxylamine types and various coupling reagents. (See M. Bodanszky Principles of Peptide Synthesis, Springer Verlag, N.Y., 1984). In addition to being reactive with amino groups and suitable for peptide bond formation, these activators can activate carboxyl groups to react with other functions such as SH and OH. Specific examples of suitable activators are: acyl chlorides such as valeryl chloride, phosphorous acid chlorides, arsenous acid chlorides, phosphoric acid chlorides, pyridinium phosphoryl chlorides, acylphosphonium salts, sulfuric acid derivatives, thiol acids, leuchs' anhydrides, active esters such as phenylesters, nitrophenylesters, dinitrophenylesters, methoxyphenylesters, chlorophenylesters, fluorophenylesters, reactive hydroxylamine derivatives such as hydroxyphthalamide esters, N-hydroxysuccinimide esters, N-hydroxypiperidine esters; coupling reagents: specifically carbodiimides such as dicyclohexyl carbodiimide, ethyl-dimethylaminopropyl carbodiimide (EDC), 1-ethoxycarbonyl-2-ethoxy-1,2-dihydroquinoline (EEDQ), 1-isobutyoxycarbonyl-2-isobutyloxy-1,2-dihydroquinoline (IIDO), diphenylketenes, acyloxyphosphonium salts. Auxiliary nucleophiles can be used as additives in coupling reactions (primarily with carbodiimides) such as N-hydroxysuccinimide, 1-hydroxybenztriazole, 3-hydroxy-3,4-dihydro-1,2,3,-benztriazin-4-one (HOObt).

An important group of RDPs are those obtained with conjugands that are aromatic amines. Preferably, aromatic amines such as phenylene diamines, aminopyrimidine, naphthylamine or 5-I-2-aminopyrimidine yield RDPs that can be diazotized wherein the diazonium salt derivative can be further used for coupling suitable molecules such as proteins with phenol side groups (Example 5, Table 4). The preferred aromatic amines found particularly suitable for producing diazotizable RDPs suitable for yielding relatively high coupling of RNase or hemoglobin are 1-naphthylamine, 5-I-2-aminopyrimidin, 1,2-naphthylene diamine, 1-5-naphthylene diamine, m-phenylene diamine, and 2,6-diamino pyridine (from Table 4).

Specific examples of suitable aromatic amines that can be used for producing functionalized RDPs or diazotizable RDPs are: 2-amino azobenzene, 3-amino azobenzene, 4-amino azobenzene, 2,2'-diamino azobenzene, 2,4-diamino azobenzene, 4,4,-diamino azobenzene, 1-chloro-2,4-diaminobenzene, 1-chloro-3,5 diaminobenzene, 2-chloro-1,3-diaminobenzene, 2-chloro-1,4-diaminobenzene, 4-chloro-1,2-diaminobenzene, 1,3-diamino benzene, 1,4-diamino benzene, orthanilic acid, methanilic acid, sulfanilic acid, 3,5-diamino benzenesulfonic acid, 2-amino benzimidazole, anthranilic acid, 3-amino benzoic acid, 4-amino benzoic acid, 2,4-diamino benzoic acid, 2,5-diamino benzoic acid, 3,4-diamino benzoic acid, 3,5-diamino benzoic acid, 2-amino benzophenone, 3-amino benzophenone, 4-amino benzophenone, 2,2'-diamino benzophenone, 3,3'-diamino benzophenone, 2-amino biphenyl, 3-amino biphenyl, 4-amino biphenyl, 2,2'-diamino biphenyl, 2,4'-diamino biphenyl, 3,3'-diamino biphenyl, 4,4'-diamino biphenyl, o-benzhydraniline, m-benzhydraniline, p-benzhydraniline, 4,4'-diaminoditan, 4,4'-diaminotritan, pararosaniline, 1-naphthylamine, 2-naphthylamine, 1,2-diamino naphthalene, 1,5-diamino naphthalene, 2,6-diamino naphthalene, 1,7-diamino naphthalene, 1,8-diamino naphthalene, 2,6-diamino naphthalene, 3-amino phenanthrene, 9-amino phenanthrene, o-hydroxy aniline, m-hydroxy aniline, p-hydroxy aniline, o-acetyl aniline, m-acetyl aniline, p-acetyl aniline, p-amino phenacyl chloride, 2-amino acridine, 3-amino acridine, 4-amino acridine, 9-amino acridine, 3,6-diamino acridine, aniline, 3-acetamido aniline, 4-acetamido aniline, 2-bromo aniline, 3-bromo aniline, 4-bromo aniline, 2-chloro aniline, 3-chloro aniline, 4-chloro aniline, 2,3-dibromo aniline, 2,4-dibromo aniline, 2,5-dibromo aniline, 2,6-dibromo aniline, 3,5-dibromo aniline, 2,3-dichloro aniline, 2,4-dichloro aniline, 2,5-dichloro aniline, 3,4-dichloro aniline, 3,5-dichloro aniline, o-butyl aniline, p-butyl aniline, 4-dimethylamino aniline, o-ethyl aniline, m-ethyl aniline, p-ethyl aniline, o-phenetidine, m-phenetidine, p-phenetidine, 2-phenoxy aniline, 3-phenoxy aniline, 4-phenoxy aniline, 1-amino anthracene, 2-amino anthracene, 9-amino anthracene, 1,2-diamino anthraquinone, 1,3-diamino anthraquinone, 1,4-diamino anthraquinone, 1,5-diamino anthraquinone, 1,6-diamino anthraquinone, 1,7-diamino anthraquinone, 1,8-diamino anthraquinone, 2,3-diamino anthraquinone, 2,6-diamino anthraquinone, 2,7-diamino anthraquinone, 5-iodo-o-toluidine, 4-iodo-o-toluidine, 2-iodo-m-toluidine, 6-iodo-m-toluidine, 5-iodo-m-toluidine, 3-iodo-p-toluidine, 2-iodo-p-toluidine, 4-iodo-m-toluidine, 2,3-diamino toluene, 2,4-diamino toluene, 2,5-diamino toluene, 2,6-diamino toluene, 3,4-diamino toluene, 3-5-diamino toluene, and tyramine.

In addition to producing diazotizable RDPs, the aromatic amines listed above can also be used to produce RDPs that have other reactive properties, namely, RDPs that are reactive with carboxyl-containing compounds in the presence of activators, RDPs that are reactive with bifunctional reagents and those that are reactive with nucleophile-functionalized RDPs. In addition to amino groups, other relatively radio resistant nucleophiles or nucleophiles that survive irradiation during radiosterilization in sufficient numbers to be used for coating the plate with adequate densities of nucleophiles, for example SH or OH, can be linked to polymers to produce nucleophilized RDPs.

Conjugands that are carbohydrates or derivatives thereof can be used to derivatize polymers under irradiation and produce glycophase RDPs. The term glycophase RDP as used herein refers to a solid support carrying vicinal diols, usually in the form of a covalently attached carbohydrate to glass (Corning, Pierce), to Sephadex, Sepharose (Pharmacia) or other similar products. The glycophase RDPs can be activated with cyanogen bromide as shown in Ceska et al., J. Allerg. Clin. Immunol. Vol. 49, 1972, pp. 1-9 or with periodate as shown in Varga, Methods Enzymol., Vol. 112, 1985, pp. 259-269 or with other suitable activating substances. The particularly preferred conjugands used for producing glycophase RDPs are phenolalpha-D-galactosid, phenol-beta-D-galactosid and phenolbeta-D-glucosid. Additional suitable conjugands which can be used for producing glycophase RDPs include: 2-acetamido-4,6-benzylidene-2-deoxy-beta-glucopyranose, N-acetyl-beta-glucosamine naphthol, p-aminobenzyl-1-thio-2-acetamido-2-deoxy-beta-glucopyranoside, p-aminophenyl-2-acetamido-2-deoxy-1-thio-beta-glucopyranoside, p-aminophenyl-alpha-fucopyranoside, p-aminophenyl-alpha-galactopyranoside, p-aminophemyl-beta-galactopyranoside, p-aminophenyl-alpha-glucopyranoside, p-aminophenyl-betaglucopyranoside, o-aminophenyl-alpha-glucuronide, p-amino-phenyl-1-thio-beta-glucuronide, p-aminophenyl-betalactopyranoside, p-aminophenyl-alpha-mannopyranoside, p-aminophenyl-beta-thiofucopyranoside, p-aminophenyl-1-thio-beta-galactopyranoside, p-aminophenyl-1-thio-beta-glucopyranoside, p-aminophenyl-1-thio-beta-xylopyranoside, p-aminophenyl-beta-xylopyranoside, D-amygdalin, N-benzoyl-alpha-glucosamine, benzyl 2-acetamido-6-0-(2-acetamido-2-deoxy-beta-glucopyranosyl)-2-deoxy-alpha-glucopyranoside, benzyl 2-acetamido-2-deoxy-alpha-galactopyranoside, benzyl 2-acetamido-2-deoxy-3-0-beta-galactopyranosyl-alphagalactopyranoside, benzyl 2-acetamido-2-deoxy-alphaglucopyranoside, benzyl-2-acetamido-2-deoxy-betaglucopyranoside, benzyl 2-acetamido-2-deoxy-3-0-betaglucopyranoside, benzyl-N-CBZ-glucosamidine, benzyl-4-0-beta-galactopyranosyl-beta-glucopyranoside, 4,6-0benzylideneglucopyranoside, 4,6-0-benzylideneglucose, 6-bromo-2-naphthylgalactopyranoside, 6-bromo-2-naphthylglucopyranoside, 6-bromo-2-naphthylglucopyranoside, n-butyl 4-O-galactopyranosyl-beta-glucopyranoside, 6,7-dihydroxycoumarin-6-glucoside, n-dodecyl beta-glucopyranoside, n-dodecyl beta-maltoside, esculin, fluorescein di-(betagalactopyranoside), beta-galactose naphthol, heptanoyl-N-methylglucamide, n-heptyl beta-glucopyranoside, hesperidin, 2-hexanedecanoylamino-4-nitrophenyl-betagalactopyranoside, 2-hexadecanoylamino-4-nitrophenyl-beta-glucopyranoside, n-hexyl-beta-glucopyranoside, 8-hydroxyquinoline-betaglucopyranoside, 8-hydroxyquinoline glucuronide, mandelonitrile-betaglucoside, mandelonitrile glucuronic acid, alpha-naphthyl-alpha-galactopyranoside, alphanaphthyl-betagalactopyranoside, beta-naphthyl-betagalactopyranoside, beta-naphthyl-alpha-glucopyranoside, beta-naphthyl-beta-glucopyranoside, beta-naphthyl-alphaglucoside, alpha-naphthyl-beta-glucuronide, naringin, nnonyl glucoside, n-nonyl glucopyranoside, octadecylthioethyl 4-O-alpha-galactopyranosyl-beta-galactopyranoside, octanoyl-N-methylglucamide, n-octyl alphaglucopyranoside, n-octyl-beta-glucopyranoside, phenolphthalein glucuronic acid, phenolphthalein mono-beta-glucosiduronic acid, phenolphthalein mono-beta-glucuronic acid, phenyl-2-acetamido-2-deoxy-alpha-galactopyranoside, phenyl-2-acetamido-2-deoxy-alpha-glucopyranoside, alpha-phenyl-N-acetylglucosaminide, beta-phenyl-N-acetylglucosaminide, phenylethyl-beta-galactoside, phenyl-beta-galactoside, phenyl-beta-galactopyranoside, phenyl-alpha-glucopyranoside, phenyl-beta-glucopyranoside, phenyl-alpha-glucoside, phenyl-beta-glucoside, phenyl-beta-glucuronide, phenyl-alpha-mannopyranoside, phenyl-beta-thiogalactopyranoside, phenyl-beta-thiogalactoside, and salicin.

By using carboxyl-containing compounds as the conjugand, a carboxylated RDP can be produced, which can be further activated with carbodiimides or other suitable activators recited herein. For, the activation of solid phase-bound carboxyls, see Sott, L. T., et al., (J. Am. Chem. Soc., Vol. 99, 1977, pp. 625-626). The term carboxyl-containing compound as used herein means conjugands that contain at least one carboxyl group and at least one aromatic structure in the same molecule, but not necessarily aromatic carboxyls. Examples of the particularly preferred carboxyl-containing conjugands are benzoic acid, naphthoic acid and its derivatives, phenyl acetic acid and phenyl naphthoic acid and its derivatives. Additional carboxylcontaining compounds which can serve as conjugands for producing carboxylated RDPs include: acetic acid, o-bromotoluic acid, m-bromo-toluic acid, o-chloro-toluic acid, m-chlorotoluic acid, p-chloro-toluic acid, homogentisic acid, diphenyl acetic acid, benzylic acid, phenyl glycolic acid, o-hydroxy-alpha-toluic acid, m-hydroxy-alphatoluic acid, p-hydroxy-alpha-toluic acid, thioglycolic acid, methoxyphenyl acetic acid, 1-naphthoxy acetic acid, 2-naphthoxy acetic acid, 1-naphthalene acetic acid, N-benzoyl aspartic acid, o-azobenzoic acid, m-azobenzoic acid, p-azobenzoic acid, phthalic acid, isophthalic acid, terephthalic acid, 2-amino-1,3-benzene dicarboxylic acid, 4-amino-1,3-benzene dicarboxylic acid, 5-amino-1,3-benzene dicarboxylic acid, 2-amino-1,4-benzene dicarboxylic acid, 4-amino-1,4-benzene dicarboxylic acid, 5-amino-1,4-benzene dicarboxylic acid, hemimellitic acid, trimellitic acid, trimesic acid, benzoic acid, 2-chloro-benzoic acid, 3-chloro-benzoic acid, 4-chloro-benzoic acid, anilino acetic acid, N-benzoyl leucine, N-benzoyl lysine, 1-naphthoic acid, 2-naphthoic acid, 1,2-naphthalene dicarboxylic acid, 1,4-naphthalene dicarboxylic acid, 1,5-naphthalene dicarboxylic acid, 1,6-naphthalene dicarboxylic acid, 1,7-naphthalene dicarboxylic acid, 1,8-naphthalene dicarboxylic acid, 2,3-naphthalene dicarboxylic acid, 2,6-naphthalene dicarboxylic acid, 2,7-naphthalene dicarboxylic acid, 2-phenyl pentane dioic acid, valerianic acid, 1-phenanthrene carboxylic acid, 2-phenanthrene carboxylic acid, 3-phenanthrene carboxylic acid, phthalic acid, proline, propionic acid, 2,2-diphenyl propionic acid, 2,3-diphenyl propionic acid, 3,3-diphenyl propionic acid, 2,3-diphenyl-2-hydroxy propionic acid, 3,3-diphenyl-2-hydroxy propionic acid, 3,3-diphenyl-3-hydroxy propionic acid, benzoyl glycolic acid, alpha-hydroxyhydrocynnamic acid, 3-hydroxy-2-phenyl propionic acid, 3-hydroxy-3-phenyl propionic acid, melilotic acid, 2-methyl-3-phenyl-propionic acid, 3(1-naphthyl)-propionic acid, 3(2-naphthyl)-propionic acid, phenyl pyruvic acid, benzoyl acetic acid, 2-phenoxy propionic acid, 3-phenoxy propionic acid, 2-phenyl propionic acid, 3-phenyl propionic acid, picolinic acid, nicotinic acid, isonicotinic acid, quinolinic acid, lutidinic acid, dipicolinic acid, dinicotinic acid and benzyl succinic acid.

Protein modifying reagents that are known in the art (See Lundblad, L. L., Noyes, C. M.: Chemical reagents for protein modification, CRC Press, Boca Raton, 1984) can serve as conjugands for producing RDPs that are nucleophilereactive polymers. The preferred protein-modifying reagents are those protein modifying reagents that contain at least one protein reactive group and at least one aromatic structure such as Bolton-Hunter reagent, OPA, TNBSA, Dansyl chloride, Dabsyl chloride, DABITC, SBF-chloride, Ellman's reagent, p-hydroxyphenylglyoxal, BTI, Ninhydrin, (See Pierce 1988 Handbook for the abbreviations) or fluorescamin, FITC, RITC FLUOS, RESOS, RHODOS, and Resornfin from Sigma Co. Additional suitable protein-modifying reagents are previously recited herein under conjugands for making reactive RDPs.

Bi-functional reagents can be used to react with functionalized RDPs, specifically nucleophile-functionalized RDPs and RDPs formed from conjugands that contain amino groups or water. The term bi-functional reagent as used herein refers to cross-linking reagents that are capable of combining or bridging the RDP with at least one ligand. The term bi-functional reagents includes polyfunctional reagents or "cross-linking" reagents that contain multiple functional groups. The preferred bi-functional reagents are EDC, BDE and TDI (See Table 5). Additional examples of bi-functional or cross-linking reagents used in this invention include: dialdehydes, preferably glutaraldehyde, diisothiocyanates, preferably phenylene 1,4-diisothiocyanate, diisocyanates, preferably toluylene 2,4-diisocyanate, bis diazo benzidines, bis diazo-o-anisidine, biepoxides and chloro-5-triazines.

An important aspect of this invention is that there is substantial overlap between the different classes of conjugands used to make the different classes of RDPs. For example, the conjugand p-aminophenol is both an aromatic amine which can be diazotized and it can also be turned into a quinone, which explains why this particular conjugand can be used to produce functionalized RDPs and reactive RDPs. Aromatic amine conjugands are diazotizable and, at the same time, they are nucleophile-containing; thus, in addition to diazotization, they are functionalized, suitable for coupling with bifunctional reagents and activators. Similarly, some of the reactive RDPs can also serve as functionalized RDPs.

It has been found that conjugands containing aromatic structures yield higher levels of incorporation into polystyrene than aliphatic conjugands. (Example 1, Table 1). Accordingly, aromatic compounds are preferred conjugands for radio-derivatization of polystyrene. In principle, this need not apply to other polymers such as polyethylene.

One of the simplest RDP products in this invention is formed with water as the conjugand. As shown in Table 2, relatively large amounts of water incorporate into polystyrene during radio-derivatization. The reactivities of the polystyrene-water RDP are suggestive of the formation of reactive nucleophiles (Example 7-11). They are able to form covalent bonds with DNP-aminoacids in carbodiimide-mediated reactions, and the immobilized ligand can be used in highly reproducible immunoassays (Example 22). Additionally, water-RDPs are also formed as side products when radio-derivatization is carried out in aqueous solutions.

The RDPs produced in this invention have many applications. They can be used, for example, "as such," without further modifications, for example, as substrates for cell cultures with improved adherence and growthsupporting properties, or as sorbents for chromatography using, for example, radio-aromatized, radio-alkylated, radio-carboxylated, particles. These RDPs can be especially useful when non-suppressible materials are needed, for example, for HPLC and high-performance affinity chromatography.

Reactive and functionalized RDPs have a number of applications. A large number of molded polymers, mainly polystyrene and its co-polymers, can be produced to be used as microtiter plates, tissue culture plates or pipettes. The adsorptive binding and/or reactive characteristics of these products can be favorably modified by radio-derivatization, followed by immobilization of suitable ligands. In comparison with the methods currently in use, the present method of radio derivatization has quite obvious advantages when transparent support materials are needed (microtiter plates, tissue culture labware) and when these products are exposed to high energy irradiation for the purpose of sterilization. In this case, RDPs with favorable adsorptive and/or covalent binding capacities can be obtained with relatively little extra manufacturing efforts other than irradiation used for radio-sterilization. The resulting RDPs can then be used for several applications 1) The method is generally suitable for the production of polymeric surfaces with covalently attached ligands for binding assays, including immunoassays. The method can be especially advantageous for colorimetric assays, since the optical transparency of RDPs is unimpaired. In addition, the method can be favorably considered for other types such as radiometric or fluorometric assays because of the lowbackground noise supports obtainable by radio-derivatization. 2) RDPs can be used for the covalent attachment of adhesions—molecules, antibodies, or biologically active molecules for mass cultivation of cells and panning. 3) Radio-derivatized polymers in foil and/or sheet form can be used for blotting and hybridizations. 4) Radio-derivatized polymer particles (such as polystyrene "latex" beads) can be used for the preparation of affinity sorbents, ion-exchangers or hydrophobic sorbents, that are insensitive to bases and non-suppressible, thus being suitable for HPLC columns; "reactive polymers" for organic synthesis; solid support for peptide-, oligonucleotide- and oligosaccharide synthesis; immobilized enzymes for "enzyme reactors"; immobilized antigens for the production of vaccines; immobilized transporters. 5) RDPs in liquid, gel or granular forms can be used as drug carriers. 6) The method of radio-derivatization can be considered for the preparation of molecular printed circuits in the manufacturing of microchips.

The types of molecules, particles or substances that are immobilized in the applications described above are referred to herein as ligands. The ligands in the present invention can be organic or inorganic substances. To exemplify and without any limitation thereof, additional ligands which can be immobilized, fixed or further linked onto the radio-derivatized polymers produced in this invention include cofactors, coenzymes, chelators, ions, hormones, drugs, dyes, lipids, lectins, carbohydrates, nucleic acids, enzymes, haptens, antigens, allergens, antibodies, viruses, microorganisms, eukaryotic cells and components thereof.

In the immobilization of ligands on RDPs with crosslinkers and activating agents, the standard methods of coupling of ligands and proteins to carbohydrate-based (e.g., "Sepharose") or polyacrylamide, and other (e.g., inorganic) supports are generally known in the art. The following main types of covalent coupling methods can be considered, depending on the nature of the functionalized RDP and the ligand to be immobilized: a) Carboxylcontaining molecules can be converted into nucleophilereactive derivatives (i.e., with carbodiimide) and exposed to nucleophilised RDP (Example 4, FIG. 2). The same method can be used with proteins (Example 6, Table 5). Considering this general method, other reagents, such as symmetric or mixed acid anhydrides, Leuch's anhydrides, acid azides, or reactive hydroxylamine derivatives can be used. The yield of these types of coupling reactions can be increased with the inclusion of "helper nucleophiles" such as 1-hydroxybenzotriazol, other benzotriazine derivatives and hydroxysuccinimide, etc.; b) Diazonium salt-reactive (e.g., phenol-RDPs can be used for coupling diazotized molecules; c) Homo- or heterobifunctional cross-linkers can be used that are able to react with functional groups present on the RDPs and the molecules to be immobilized (Table 2); d) RDPs can be further modified with "spacers" using Leuch's anhydrides, beta-alanin, oligoglycine, etc., using e.g., amino-functionalized RDPs and amino-blocked spacers. The amino-spacer-RDP can be obtained after deblocking.

This invention is not limited to the coupling methods discussed above, as numerous other methods known in the art can be used for coupling molecules to functionalized RDPs.

The resulting RDPs formed by the conjugand and the polymer and the final RDPs linked to ligands can be identified by radiometry by using radiolabelled conjugands (Example 1, Table 1). Radio-labelled ligands or ligandbinding proteins (FIG. 2, Tables 3-5) can be used to identify the ligand-binding protein to the RDP. Other methods known in the art can also be used.

Although all types of polymers containing radiolysable bonds can be used for radio-derivatization, the preferred embodiment of this invention and all the examples described below have been carried out with polystyrene. The conjugands were added to polystyrene (PS) microtiter plates (non-sterile unirradiated, obtained from the Greiner GmbH, Kremsmunster, Austria; 100 μl/well) 100 mM (unless noted otherwise) in water (pH 9, NaOH). The plates were sealed with adhesive foil (Nunc No 236269) and hermetically packed with a polyethylene foil heat sealer (Krups Co., FRG), then exposed to a gamma source as described above. Nonirradiated (control) plates were kept at room temperature for the same length of time with the same substances as the irradiated ones and subsequently processed the same way as the irradiated plates. The solutions were removed from the plates by vigorous shaking and the plates were washed in sequence: 10 times with tap water, then 200 μl NaHCO$_3$ (0.1M) was added and kept at room temperature for 5 minutes, the solution was removed and 200 μl KCl (2M in glycine buffer (0.2M, pH3) was added and kept at room temperature for 15 minutes; the last two washing steps were repeated four times followed by washing 10 times with tap water and twice with distilled water; the plates were used immediately for binding studies or they were stored in a vacuum at room temperature. Under these conditions there was no significant loss of reactivity in one month.

Conjugands that are known in the art to hydrolyze, or otherwise react with water under conditions of radio-derivatization, necessitate an alternative washing procedure. The plates should be washed five times with anhydrous formamide following radio-derivatization, instead of the above aqueous washing procedures, and used immediately for immobilization of molecules. General examples of conjugands that would hydrolyze under the conditions of radio-derivatization (in acqueous alkaline solution) are acid anhydrides, acid halides, isothiocyanantes, carbodiimides, oxyranes and nitro-aromatic halides.

Conjugands that hydrolyze in water are used preferably in undiluted form when the conjugand is liquid at room temperature. Both liquid and solid hydrolyzable conjugands can be used in solution in anhydrous formamide or other solvents, such as DMSO, which do not dissolve the polymer, i.e., polystyrene, and do not lyse the conjugand.

Generally, conjugands that do not hydrolyze are used preferably in aqueous, alkaline solution, but can also be used in solution with solvents other than water, provided such solvents do not dissolve the polymer (i.e., polystyrene) and do not lyse the conjugand, such as formamide. Non-hydrolyzable conjugands that are in liquid state at room temperature can also be used in undiluted form. The use of liquid non-hydrolyzable conjugands in undiluted form is preferred when the conjugand has low solubility in water and/or formamide. Among the examples disclosed herein, 1,3-diamino-2-hydroxy propane was used in undiluted form.

The uptake of radiolabeled conjugands was measured using the same procedure of radio-derivatization discussed above with the following modifications: 0.1-3 μCi of radiolabeled conjugand was added as a tracer to the unlabeled substance and following irradiation and the washing steps the wells of microtiter plates were cut out with a red-hot razor blade, solubilied with Bioflour (NEN) emulsifier cocktail and counted in a liquid scintillation counter (LKB/Wallac 1215).

Irradiation was performed using A$^{60}$Co. gammasource (ca. 17 000 Ci) with an intensity of 0.1-0.2-Mrad/h to a total dose of 1-15Mrad, preferably 3-5Mrad, at normal atmospheric pressure, at room temperature. Exclusion of oxygen during irradiation generally has a favorable effect on the reactivity of RDPs. However, even if irradiation in the presence of oxygen yields RDPs with lower reactivity, they are sufficiently reactive for the immobilization of ligands for immunoassays, See Example 22. Although the above gamma-source type of irradiation was used in the Examples herein, any type of high-energy irradiation (i.e. electron-radiation) that is capable of radiolysing the polymer and/or conjugand can be used in this invention.

Ethyldiethylaminopropyl-carbodiimide or EDC-mediated coupling was performed for small molecules by adding 50 μl solutions (2 mM in NaCl, 0.1M, pH 5, or pH 3 for DNP-Gly) of the molecules to be coupled to the wells of radio-derivatized microtiter plates followed by 50 μl EDC solution (2 mg/ml in NaCl, 0.1M, pH 5 or pH 3 for DNP-Gly). The coupling was allowed to proceed at room temperature for two hours in the dark with light sensitive materials; nonbound material was removed by washing and the uptake of labeled compounds was measured.

For EDC-mediated coupling of proteins 1 mg/ml protein solutions with approximately 100,000 cpm trace-[$^{125}$I] labeled proteins were used at room temperature for two hours in the dark with light sensitive materials and with 10 mg/ml EDC solution, pH adjusted to 5. The non-bound proteins were removed as described above except that washing solutions were supplemented with 0.05% Tween 20 and PBS was used instead of the KCl/glycine solution. The radioactivity was counted in a gamma counter (LKB/Wallac CliniGamma). The proteins were labeled with $^{125}$I using the "Enzymobead" method of Bio Rad, Richmond, Calif.

Diazo-coupling was obtained by the following procedure: Radio-derivatized (and control) plates were pre-cooled on ice-water for 30 minutes; ice cold NaNo$_2$ solution (5 mg/ml in 2N HCl) was added and kept on ice-water for one hour. The liquid was removed and the plate was washed three times with ice cold water. 100 μl protein solution [1 mg/ml (+0.1 μCi trace-labeled protein) in borate buffer (0.1M, pH 8.5)] was added to the wells and the coupling was allowed to take place overnight at 4° C. Non-bound protein was removed; the plates were washed and the uptake of proteins was determined as described above.

Coupling with cross-linkers was obtained by pretreating the radio-derivatized plates with bifunctional reagents [100 μl/well, 25 mg/ml in phosphate buffer (0.2M, pH 7.2)] for two hours at room temperature. The reagents were removed and the protein solutions containing tracelabeled proteins were added. Coupling was allowed to continue overnight at 4° C. The non-bound proteins were removed and the amount of bound substance was measured as described above.

The above methods and materials can be altered without departing from the spirit and scope of the invention or sacrificing its advantages. The following Examples merely illustrate and do not limit the invention.

EXAMPLE 1

Commercially available radiochemicals (listed in Table 1) in amounts of 2–5 μCi/50 μl/well, diluted with 1–100 mM cold substance in aqueous solutions (pH 9, NaOH) were added to non-irradiated (Greiner No. 651 101) microtiter plate wells and the wells were sealed with plate adhesive foil (Nunc No. 236 269). In addition, the plates were sealed individually with a polyethylene foil heat sealer and irradiated with $^{60}$Co gamma-source (Ca. 17000 Ci) with an intensity of 0.1–0.2 Mrad/h to a total of 1–15Mrad, preferably 3–5Mrad, at normal atmospheric pressure at room temperature. The nonirradiated (control) plates containing the same substances were kept at room temperature for the same length of time as the irradiated plates and subsequently processed the same way as the irradiated plates. Following irradiation the contents of the wells were removed with adsorbing paper and the plates were washed in the following sequence: 10 times with tap water, then 200 μl NaHCO$_3$ (0.1M) was added and kept at room temperature for 5 minutes, the solution was removed and 200 μl KCl (2M in glycine buffer) (0.2M, pH3) was added and kept at room temperature for 15 minutes. The last two washing steps were repeated four times followed by washing 10 times with tap water and twice with distilled water. The plates were dried on air; the wells were cut out with a red-hot razor blade, solubilized with "Biofluor" (NEN) emulsifier cocktail and counted in an LKB/Wallac 1215 liquid scintillation counter. The results are shown in Table 1.

TABLE 1

Radiation-mediated uptake of radiochemicals by polystyrene

| | CONDITIONS | | |
|---|---|---|---|
| | non-irradiated | irradiated | |
| SUBSTANCE | uptake nmoles/well (S.D.) | | F(RC)$^+$ |
| [3H]Na-acetate | 2.60(0.36) | 3.90(1.02) | 1.5 |
| [2-3H]glycine | 0.80(0.09) | 2.80(0.70) | 3.5 |
| L-[4,5-3H]lysine | 2.90(0.27) | 3.77(0.85) | 1.3 |
| [5,6(n)-3H]prostaglandinE1 | 1.55(0.13) | 1.86(0.46) | 1.2 |
| [1,4(n)-3H]putrescine | 0.25(0.06) | 2.78(0.75) | 11.1 |
| [3-[5(n)-3H]indolylacetate | 1.10(0.22) | 2.30(0.67) | 2.1 |
| Benzyl[14C]penicillin | 0.60(0.06) | 11.22(2.86) | 18.7 |
| [7-14C]benzoic acid | 0.75(0.09) | 38.85(5.5) | 51.8 |
| [7-14C]salicylic acid | 0.80(0.14) | 23.20(0.67) | 29.0 |

$^+$F(RC): factor of radio-derivatization = uptake(irradiated)/uptake(non-irradiated)

EXAMPLE 2

Polystyrene-water RDP

To anhydrous formamide, dimethylsulfoxide or to H$_2$O, tritiated water (sp. RA ca 2000 Ci/ml) was added in increasing concentrations; plates containing 20 μl/well solutions were irradiated, processed and covalently bound [3H] was measured as described in Example 1; non-irradiated control plates were exposed to the same solutions for the same length of time as irradiated plates. The results are shown in Table 2.

TABLE 2

| | Radiation-mediated uptake of [3H]-H$_2$O | | |
|---|---|---|---|
| | IRRADIATED | NON-IRRADIATED | |
| SOLVENT | Uptake$^{++}$ of [3H] (nmoles/well) | | F(RC)$^+$ |
| DMSO | 350 | 1.3 | 269 |
| Formamide | 378 | 3.7 | 102 |
| H$_2$O | 293 | 1.6 | 183 |

$^+$F(RC): Factor of radioconjugation = (irradiated/non-irradiated) uptake of [3H]-H$_2$O
$^{++}$at saturation

EXAMPLE 3

Coupling of proteins to reactive RDPs

Conjugands listed in Table 3 (10 mg/ml solutions in 1 mM NaOH) were added to microtiter wells and processed as described in Example 1; $^{125}$I RNase or $^{125}$I hemoglobin were diluted with 1 mg/ml unlabeled proteins in borate buffer (0.1M, pH 8.5), 100 μl/well were added to microtiter plates and kept for sixteen hours at 4° C.

The non-bound proteins were removed as described in Example 2 except that washing solutions were supplemented with 0.05% Tween 20 and PBS was used instead of KCl/glycine solution. The uptake of proteins were calculated from the total counts added to the wells. The results are shown in Table 3.

TABLE 3

Coupling of proteins to reactive RDPs

| CONJUGAND | NON-IRRADIATED | | IRRADIATED | |
|---|---|---|---|---|
| | RNase | Hemoglobin | RNase | Hemoglobin |
| | Uptake of proteins % | | | |
| None | 0.0 | 0.1 | 0.3 | 0.1 |
| 7-aminoheptanol-1 | 0.0 | 0.0 | 0.0 | 0.0 |
| tryptamine | 0.1 | 0.1 | 0.5 | 0.2 |
| AHE | ND | ND | 0.5 | 0.1 |
| homarylamine | 0.1 | 0.1 | 0.4 | 0.1 |
| o-amino benzoic acid | 0.0 | 0.0 | 0.1 | 0.1 |
| p-aminophenol | 0.5 | 0.1 | 3.7 | 21.3 |
| 2-amino-4-Cl-phenol | 1.5 | 0.1 | 1.2 | 59.9 |
| 5-I-2-amino pyrimidine* | 0.0 | 0.0 | 4.4 | 0.8 |
| o-phenylene diamine | 0.6 | 0.2 | 1.5 | 0.4 |
| m-phenylene diamine | 1.4 | 0.2 | 3.7 | 1.6 |
| m-toluylene diamine | 0.8 | 0.2 | 2.1 | 0.6 |
| 2,6-diamino pyridine | 0.7 | 0.1 | 2.9 | 0.2 |
| 3-O-azo-diamino pyridine | 0.0 | 0.0 | 1.7 | 0.1 |
| 1-naphthylamine* | 0.1 | 0.1 | 1.1 | 0.9 |
| 2-naphthylamine | 0.1 | 0.1 | 0.5 | 0.2 |
| 1,2-naphthylene diamine* | 1.4 | 0.2 | 4.6 | 0.7 |
| 1,8-naphthylene diamine | 2.0 | 0.3 | 4.9 | 0.4 |

AHE = DL-2-amino-1(4-Hydroxyphenyl)-ethanol-1
* = optical quality of PS was impaired during radio-derivatization
ND = not determined
The numbers were rounded up to the next tenth digit with .05 cut-off limit.

EXAMPLE 4

EDC-mediated uptake of carboxylic acids by RDPs

The uptake of the following carboxylic acids was measured: A) acetic acid; B) glycine; C) DNP-glycine; D) benzoic acid; E) salicylic acid. FIG. 2 shows the effects of radio-derivatization of polystyrene on the EDC-mediated uptake of these carboxylic acids. The irradiation was carried out in the presence of the following solutions (the numbers correspond to the numbering of the x-axis in FIG. 2):

1) none;
2) $H_2O$;
3) $NH_3$, 25%;
4) ammonium sulphate, saturated;
5) ethylamine-HCl, 90%;
6) 1,3-diamino-2-hydroxy propane 99% (undiluted);
7) 1,4-diaminobutanone.2HCl 20% 1mM NaOH;
8) ethylenediamine.HCl 7.5% in 1 mM NaOH;
9) isobutylamine.HCl 4% in 1 mM NaOH;
10) DL-2-amino-1(4-hydroxyphenyl)-ethan-1-ol 4% in 1 mM NaOH;
11) 1,6-diamino hexan 14% in 1 mM NaOH;
12) p-aminophenol 4% in 1 mM NaOH;
13) 3,4-diamino pyridine 3.3% in 1 mM NaOH;
14) L-alanine benzyl ester 3.3% in 1 mM NaOH;
15) L-serine benzyl ester 4.4% in 1 mM NaOH;
16) galactosamine 11% in $H_2O$.

The results are shown in FIG. 2. In Chart (a) shaded histograms show uptake of radioactivity without EDC while non-shaded histograms show uptake of radioactivity with EDC. Lower Chart (b) shows the relative uptake: ratio of uptake obtained with irradiated plates versus nonirradiated plates in the presence of EDC. To summarize, the results in FIG. 2 show that polystyrene microtiter plates irradiated in the presence of aromatic amines such as p-aminophenol, AHE, L-alanine and benzyl ester become reactive with acetic acid, DNP-Gly or benzoic acid in EDC-mediated reactions. No significant EDC-mediated fixation was observed with glycine (B), most probably because of peptide bond formation as the favored reaction. Low coupling densities were obtained with salicylic acid (E) except with L-alanine benzyl ester-conjugated plates. The selfreactivity of the phenolic hydroxyl in salicylic acid with the mixed EDC-carboxyanhydride derivative may explain the failure of EDC-mediated coupling of this substance to polystyrene.

EXAMPLE 5

Coupling of proteins to diazotized RDPs

Radio-derivatizations were carried out with conjugands listed in Table 4 as described in Example 2. They were diazotized according to the following procedure: Radio-derivatized (and control) plates were precooled in ice-water for 30 minutes. Ice cold $NaNO_2$ solution (5 mg/ml in 2N HCl) was added and kept in ice-water for 1 hour. The liquid was removed and the plate was washed three times with ice cold water. 100 μl protein solution [1 mg/ml (+0.1 μCi tracelabeled RNase and hemoglobin protein) in borate buffer (0.1 M, pH 8.5)]was added to the wells and the coupling was allowed to take place overnight at 4.C; non-bound protein was removed; the plates were washed as described in Example 3 and the uptake of proteins was determined as described in Example 2. The results are shown in Table 4.

TABLE 4

Coupling of proteins to diazotized radioconjugates

| CONJUGAND | NON-IRRADIATED | | IRRADIATED | |
|---|---|---|---|---|
| | RNase | Hemoglobin | RNase | Hemoglobin |
| | Uptake of proteins % | | | |
| None | 0.0 | 0.1 | 0.2 | 0.1 |
| 7-aminoheptanol-1 | 0.0 | 0.0 | 0.0 | 0.0 |
| tryptamine | 0.3 | 0.2 | 0.8 | 0.2 |
| AHE | ND | ND | 0.7 | 0.1 |

TABLE 4-continued

| | Coupling of proteins to diazotized radioconjugates | | | |
|---|---|---|---|---|
| | NON-IRRADIATED | | IRRADIATED | |
| CONJUGAND | RNase | Hemoglobin | RNase | Hemoglobin |
| | | Uptake of proteins % | | |
| Homarylamine | 0.1 | 0.2 | 0.3 | 0.2 |
| o-amino benzoic acid | 0.0 | 0.0 | 0.1 | 0.1 |
| 5-I-2-amino pyrimidine* | 0.1 | 0.1 | 21.8 | 1.5 |
| o-phenylene diamine | 1.5 | 0.2 | 3.1 | 0.7 |
| m-phenylene diamine | 2.4 | 0.3 | 8.4 | 1.8 |
| m-toluylene diamine | 0.8 | 0.2 | 1.9 | 0.3 |
| 2,6-diamino pyridine | 1.7 | 0.1 | 4.9 | 0.3 |
| 3-O-azo-diamino pyridine* | 0.1 | 0.1 | 5.0 | 0.3 |
| 1-naphthylamine* | 0.4 | 0.2 | 40.8 | 6.2 |
| 2-naphthylene diamine* | 0.2 | 0.1 | 1.3 | 0.2 |
| 1,2-naphthylene diamine | 1.8 | 0.2 | 5.2 | 0.7 |
| 1,5-naphthylene diamine | 2.6 | 0.2 | 9.6 | 0.6 |

AHE = DL-2-amino-1 (4-hydroxyphenyl)-ethanol-1
*Optical quality of PS was impaired during radio-derivatization
ND = not determined
The numbers were rounded up to the next tenth digit with 0.05 cut-off limit.

EXAMPLE 6

Coupling of proteins to p-aminophenolpolystyrene RDP with EDC and bifunctional reagents P-aminophenol-polystyrene RDP was prepared and processed as described in Example 2. Bifunctional reagents listed in Table 5, namely, ethyldiethylaminopropyl-carbodiimide (EDC); 1,4-butandiol diglycidyl ether (BDE); toluylen-2,4-diisocyanate (TDI) were added to microtiter wells (100 μl/well, 25 mg/ml in K-phosphate buffer (0.2M, pH 7.2). The plates were kept at room temperature for one hour. The coupling solutions were shaken out and residue removed by impacting on adsorbing paper over a hard surface. Tracelabeled proteins (100 μl/well) were added immediately and kept at 4° C. for sixteen hours and uptake of proteins were measured as described in Example 3. For EDC-mediated coupling 50 μl trace-labeled proteins were added to the wells followed by 50 μl EDC solution (10 mg/ml in 0.1M NaCl, pH 5); the plates were sealed with adherent tape, kept at room temperature for four hours and uptake of proteins was determined as described above. The results are shown in Table 5.

TABLE 5

| | Coupling of proteins to p-aminophenol-PS RDP | | | | |
|---|---|---|---|---|---|
| PLATE TREATMENT | COUPLING REAGENT | MYOSIN | HEMOGLOBIN | PEPSIN | RNase |
| | | | Uptake of Proteins % | | |
| p-amino- | 0 | 2.0 | 21.3 | 0.8 | 3.7 |
| phenol- | EDC | 2.5 | 60.1 | 33.2 | 0.0 |
| derivatized | glutarald. | 3.0 | 2.0 | 0.3 | 0.2 |
| | epichl.hdr. | 3.1 | 3.1 | 0.0 | 0.0 |
| | BDE | 2.3 | 1.0 | 0.2 | 0.3 |
| | TDI | 8.7 | 17.1 | 9.3 | 10.6 |
| non-irra- | 0 | 0.0 | 0.0 | 0.0 | 0.0 |
| diated | EDC | 0.0 | 0.5 | 0.0 | 0.9 |
| control | glutarald. | 0.0 | 0.2 | 0.0 | 0.1 |
| | epichl.hdr. | 0.4 | 0.0 | 0.0 | 0.0 |
| | BDE | 0.0 | 0.0 | 0.0 | 0.0 |
| | TDI | 1.1 | 1.0 | 1.5 | 1.0 |

The numbers were rounded up to the next digit with 0.05 cut-off limit.

EXAMPLE 7

EDC-mediated coupling of Penicillin G to waterpolystyrene RDP

Polystyrene microtiter plates were irradiated in a watercontaining atmosphere as described in Example 1. Penicillin G (2 mM unlabeled +0.1 μCi [14C] penicillin G in 50 μl 0.1M NaCl, pH 3) and the same volume of EDC (1 mg/ml in 0.1M NaCl, pH 3) was added and kept at room temperature for two hours. The nonbound penicillin G was removed and the plates were processed as described in Example 1. Coupling densities in the range of 50–100 pmole penicillin $G/cm^2$ were obtained.

EXAMPLE 8

EDC-mediated coupling of DNP-aminoacids to waterpolystyrene RDP

Microtiter plates were radio-derivatized as described in the previous example. DNP-glycine (1 mM+0.1 μCI DNP[3H]glycine in 50 μl 1 0.1M NaCl, pH 3) and the same volume of EDC (1 mg/ml in 0.1M NaCl, pH 3) were incubated in the microtiter plate wells at room temperature for at least one hour. The nonbound DNP-glycine was removed and the plates were processed as described in Example 1. Coupling densities ranged between 100–150 $pmoles/cm^2$.

EXAMPLE 9

Coupling of myosin to water-polystyrene RDP with oxyranes

Microtiter plates were activated as described in the previous example. They were then incubated with BDE (25 mg/ml, in 100 μl phosphate buffer, pH 7.2) for one hour. The coupling solution was removed; myosin (1 mg/ml+0.1 μCi $^{125}I$ myosin in 100 μl phosphate buffer pH 7.2) was added and coupling was allowed to take place for fourteen to sixteen hours at 4° C. The nonbound myosin was removed and the plates were processed as described in Example 3. The coupling densities ranged between 20-30 pmol myosin/cm$^2$.

EXAMPLE 10

Coupling of myosin to water-polystyrene RDP with TDC

The same method was used as described in the previous Example, but TDC was used instead of BDE. Coupling densities in the range of 15-20 pmoles myosin/cm$^2$ were obtained.

EXAMPLE 11

Coupling of RNase to water-polystyrene RDP with TDC

The same method was used as described in Example 10, but RNAse [+$^{125}$I-RNAse] was used instead of myosin. The obtainable coupling densities ranged between 2-2.5 nmoles of RNase/cm$^2$.

EXAMPLE 12

Coupling of hemoglobin to p-aminophenylpolystyrene RDP

Para-aminophenyl-polystyrene RDP was obtained as described in Example 4, and hemoglobin (1 mg/ml+0.1 $\mu$Ci $^{125}$I hemoglobin in 100 $\mu$l 0.1M NaCl, pH 3) was added and kept at room temperature for four hours. The non-bound hemoglobin was removed and the plate was processed as described in Example 3. Approximately 1 nmole hemoglobin/cm$^2$ coupling densities were obtained.

EXAMPLE 13

EDC-mediated coupling of pepsin to p-aminophenyl polystyrene RDP

Para-aminophenyl-polystyrene RDP was obtained as described in Example 4 and pepsin (1 mg/ml+0.1 $\mu$Ci $^{125}$I pepsin in 100 $\mu$l 0.1M NaCl, pH5) was added, followed by the addition of the same volume of EDC (10 mg/ml in the same solution). Following four hours of incubation at room temperature the non-bound pepsin was removed and the plate was processed as described in Example 12. Approximately 1 nmole pepsin/cm$^2$ coupling densities were obtained.

EXAMPLE 14

EDC-mediated coupling of penicillin G to paraaminophenyl-polystyrene RDP

Para-aminophenyl-polystyrene RDP was obtained as described in Example 4, penicillin G (2 mg/ml+0.1 $\mu$Ci 14C penicillin G in 100 $\mu$l 0.1M NaCl, pH 5) plus the same volume of EDC (10 mg/ml in 0.1M NaCl, pH 5) was added and kept at room temperature for four hours. The non-bound penicillins was removed and the plate was processed as described in Example 1. Approximately 3 nmoles/cm$^2$ coupling densities were obtained.

EXAMPLE 15

Coupling of RNAse to para-aminophenyl-polystyrene RDP

Para-aminophenyl-polystyrene RDP was obtained as described in Example 4; TDC was used as coupling reagent as described in Example 10; RNAse (1 mg/ml+0.1 $\mu$Ci $^{125}$I RNAse in 100 $\mu$l 0.1M borate buffer, pH 8.5) was added and kept at 4° C. for fourteen-sixteen hours. The non-bound RNAse was removed and the plate was washed and treated as described in Example 12. Approximately 1 nmole RNAse/cm$^2$ coupling densities were obtained.

EXAMPLE 16

EDC-mediated coupling of acetic acid to AHE-polystyrol RDP

AHE-polystyrol RDP was obtained as described in Example 4 and acetic acid (0.1M+0.1 $\mu$Ci [3H] acetic acid in 100 $\mu$l 0.1M NaCl, pH 5) plus the same volume of EDC (20 mg/ml in the same solution) was added and kept at room temperature for four hours. The non-bound acetic acid was removed and the plate was processed as described in Example 1. Approximately 3 nmoles acetate/cm$^2$ coupling densities were obtained.

EXAMPLE 17

EDC-mediated coupling of penicillin G to AHE-polystyrene RDP

The same method as described in the previous example was used but penicillin G (20 mM) was used instead of acetic acid. Approximately 1.5 nmoles of penicillin G/cm$^2$ coupling densities were obtained.

EXAMPLE 18

EDC-mediated coupling of benzoic acid to AHE-polystyrene RDP

The procedure described in Example 16 was followed but benzoic acid (10 mM) was used instead of acetic acid. The coupling densities ranged between 0.6-1 nmoles benzoic acid/cm$^2$.

EXAMPLE 19

EDC-mediated coupling of prostaglandin E1 to AHE-polystyrene RDP

The same procedure as described in Example 16 was followed, but prostaglandin El (1 mM) was used instead of acetic acid. The range of coupling densities were 0.5-1 nmoles prostaglandin El/cm$^2$.

EXAMPLE 20

EDC-mediated coupling of DNP-aminoacids to AHE-polystyrene RDP

The same procedure was followed as described in Example 16, but DNP-glycine (10 mM+0.1 $\mu$Ci DNP[3H]gly) was used. Approximately 5 nmoles DNP-glycine/cm$^2$ coupling densities were obtained.

EXAMPLE 21

EDC-mediated coupling of pepsin to AHE-polystyrene RDP

The same procedure was followed for the preparation of AHE-PS RDP as described in Example 16, but pepsin (1 mg/ml+0.1 $\mu$Ci $^{125}$I pepsin) was used instead of acetic acid. The plates were processed as described in Example 9. The coupling densities ranged between 0.8-1 nmoles pepsin/cm$^2$.

Example 22

Binding assay for DNP-specific IgE antibodies

Microtiter plates containing covalently bound DNP-glycine, obtained by methods described in Examples 4, 8 and 20 were used. DNP-binding mouse monoclonal IgE (trace-labeled with $^{125}$ was added and incubated at 4° C. for sixteen hours. The non-bound IgE was removed and the residual radioactivity (ranging between 30–40% of total IgE added) was determined. The intra- and inter-assay CV were under 3%. The same binding assay has been used to screen large numbers of drugs for multispecific interactions with IgE in studies on drug allergies., (Varga, J. M., Klein, G. and Fritsch, P.: J. Invest Dermatol., Vol. 92, 1989, pp. 537).

We claim:

1. A method for preparing a radio-derivatized polymer comprising contacting a radiolysable polymer and a nonpolymerizable conjugand wherein at least one of said radiolysable polymer and said conjugand is irradiated with high energy radiation, thereby linking said conjugand to said polymer by means of said irradiation.

2. The method of claim 1 wherein said radiolysable polymer is irradiated.

3. The method of claim 2 wherein said radiolysable polymer is irradiated prior to said contacting step.

4. The method of claim 1 wherein said conjugand is irradiated.

5. The method of claim 4 wherein said conjugand is irradiated prior to said contacting step.

6. The method of claim 1 wherein both said polymer and said conjugand are irradiated.

7. The method of claim 6 wherein said radiolysable polymer and said conjugand are irradiated prior to said contacting step.

8. The method of claim 6 wherein said radiolysable polymer and said conjugand are irradiated after said contacting step.

9. The method of claim 1 wherein said conjugand is selected from the group consisting of quinones, compounds from which quinones are generated under irradiation, aromatic compounds, nucleophile-containing substances, amino group-containing compounds, aromatic amine compounds, carbohydrates and derivatives thereof, carboxyl-containing compounds, protein-modifying reagents and water.

10. The method of claim 1 wherein said radiolysable polymer is polystyrene.

11. The method of claim 1 which further comprises linking said radio-derivatized polymer to a ligand selected from the group consisting of proteins, spacers, chelators, ions, cofactors, coenzymes, hormones, drugs, dyes, lipids, carbohydrates, lectins, nucleic acids, enzymes, haptens, antigens, allergens, antibodies, viruses, microorganisms, eukaryotic cells and components thereof.

12. The method of claim 1 wherein the conjugand is water and the radio-derivatized product is reactive with at least one carboxyl-containing compound in the presence of at least one activator.

13. The method of claim I wherein the conjugand is an amino group-containing compound and the radio-derivatized product is reactive with carboxyl-containing compounds in the presence of at least one activator.

14. The method of claim 1 wherein the conjugand is a nucleophile-containing substance and the product is a nucleophile-functionalized radio-derivatized polymer.

15. The method of claims 12, 13 or 14 wherein the radio-derivatized polymer is reactive with bi-functional reagents.

16. The method of claim 1 wherein the conjugand is an aromatic amine and the radio-derivatized polymer is diazotized.

17. The method of claim 1 wherein the conjugand is a carbohydrate or a derivative thereof thereby forming a glycophase radio-derivatized polymer wherein said glycophase radio-derivatized polymer is further activated.

18. The method of claim 1 wherein the conjugand is a carboxyl-containing compound and the resulting radio-derivatized polymer is further activated to react with nucleophiles.

19. The method of claim 18 wherein said carboxylated radio-derivatized product is further activated with carbodiimides to react with nucleophiles.

20. The method of claim 1 wherein the conjugand is a protein-modifying reagent and the radio-derivatized polymer is a nucleophile-reactive polymer.

21. The method of claim 1 wherein said high energy radiation is gamma radiation.

22. The method of claim 1 wherein said high energy radiation is 1–10 Mrads.

23. A radio-derivatized polymer formed by contacting a radiolysable polymer and a nonpolymerizable conjugand, wherein at least one of said radiolysable polymer and said conjugand is irradiated, thereby, linking said radiolysable polymer to said conjugand by means of said irradiation wherein said conjugand is selected from the group consisting of quinones, compounds from which quinones are generated under irradiation, aromatic compounds, nucleophile-containing compounds, amino group-containing compounds, aromatic amine compounds, carbohydrates and derivatives thereof, carboxyl-containing compounds, proteinmodifying reagents and water, with the proviso that said conjugand is capable of linking with said polymer only under high energy radiation.

24. A radio-derivatized polymer according to claim 23 wherein said linkage is formed by irradiating said radiolysable polymer prior to said contacting step with said conjugand.

25. A radio-derivatized polymer according to claim 23 wherein said linkage is formed by irradiating said conjugand prior to said contacting step with said radiolysable polymer.

26. A radio-derivatized polymer according to claim 23 wherein said linkage is formed by irradiating said radiolysable polymer and said conjugand prior to said contacting step.

27. A radio-derivatized polymer according to claim 23 wherein said linkage is formed by irradiating said radiolysable polymer and said conjugand after said contacting step.

28. A radio-derivatized polymer according to claim 23 wherein said radio-derivatized polymer is further linked to a ligand.

29. A radio-derivatized polymer according to claim 28 wherein said ligand is selected from the group consisting of proteins, spacers, chelators, ions, cofactors, coenzymes, hormones, drugs, dyes, lipids, carbohydrates, lectins, nucleic acids, enzymes, haptens, antigens, allergens, antibodies, viruses, microorganisms, eukaryotic cells and components thereof.

30. A radio-derivatized polymer according to claim 23 wherein said polymer is polystyrene.

31. A radio-derivatized polymer according to claim 23 wherein said high energy radiation is gamma radiation.

32. A radio-derivatized polymer according to claim 23 wherein said high energy radiation is 1–10 Mrads.

* * * * *